United States Patent
Sato et al.

(10) Patent No.: US 9,351,676 B2
(45) Date of Patent: May 31, 2016

(54) ELECTROCHEMICAL SENSOR, LANCET, AND BODILY FLUID MEASURING APPARATUS

(75) Inventors: Yoshiharu Sato, Kyoto (JP); Tadao Yamaguchi, Kyoto (JP); Shinichi Watanabe, Kyoto (JP); Yoshimitsu Matsuura, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/284,071

(22) Filed: Oct. 28, 2011

(65) Prior Publication Data

US 2012/0109010 A1    May 3, 2012

(30) Foreign Application Priority Data

Oct. 29, 2010 (JP) ................... 2010-243163

(51) Int. Cl.
    *A61B 5/00*     (2006.01)
    *A61B 5/1468*   (2006.01)
    *A61B 5/15*     (2006.01)
    *A61B 5/145*   (2006.01)
    *A61B 5/1486*   (2006.01)
    *G01N 27/327*   (2006.01)

(52) U.S. Cl.
    CPC ............. *A61B 5/1468* (2013.01); *A61B 5/1411* (2013.01); *A61B 5/1486* (2013.01); *A61B 5/14532* (2013.01); *A61B 2562/0295* (2013.01); *G01N 27/3271* (2013.01); *G01N 27/3272* (2013.01)

(58) Field of Classification Search
    CPC ............. A61B 5/1411; A61B 5/14532; A61B 5/1468; A61B 5/1486; A61B 2562/0295; G01N 27/3271; G01N 27/3272

USPC ................... 600/583, 573; 604/313; 156/106; 204/400, 403.14

See application file for complete search history.

(56) References Cited

U.S. PATENT DOCUMENTS

| | | | |
|---|---|---|---|
| 4,963,245 A | 10/1990 | Weetall | |
| 4,975,175 A | 12/1990 | Karube et al. | |
| 5,798,031 A * | 8/1998 | Charlton et al. | ......... 204/403.14 |
| 6,071,251 A * | 6/2000 | Cunningham et al. | ........ 600/584 |

(Continued)

FOREIGN PATENT DOCUMENTS

| | | |
|---|---|---|
| EP | 1 426 758 A1 | 6/2004 |
| JP | 2000-000231 A | 1/2000 |

(Continued)

OTHER PUBLICATIONS

The Office Action issued by the Korean Intellectual Property Office on Apr. 19, 2013, which corresponds to Korean Patent Application No. 10-2011-0111175 and is related to U.S. Appl. No. 13/284,071.

(Continued)

*Primary Examiner* — Devin Henson
(74) *Attorney, Agent, or Firm* — Studebaker & Brackett PC

(57) ABSTRACT

An electrochemical sensor includes a base plate provided with a concave part formed on one of surfaces thereof, a fluid channel formed so that a bottom part of the concave part and the other one of the surfaces of the base plate are communicated with each other, a plurality of electrodes formed on the concave part; a reagent fixed on the electrodes, a cover which covers the concave part, and an air channel which causes the inside and outside of the concave part to be communicated with each other.

14 Claims, 11 Drawing Sheets

(56) References Cited

U.S. PATENT DOCUMENTS

| | | | |
|---|---|---|---|
| 6,287,451 B1* | 9/2001 | Winarta et al. | 205/777.5 |
| 6,805,780 B1 | 10/2004 | Ryu et al. | |
| 7,640,047 B2* | 12/2009 | Sakata | A61B 5/1411 |
| | | | 204/403.1 |
| 7,785,271 B2* | 8/2010 | Fujiwara | A61B 5/14532 |
| | | | 600/583 |
| 2003/0212344 A1* | 11/2003 | Yuzhakov et al. | 600/583 |
| 2004/0116829 A1 | 6/2004 | Raney et al. | |
| 2005/0123443 A1 | 6/2005 | Fujiwara et al. | |
| 2009/0043227 A1 | 2/2009 | Fujiwara et al. | |
| 2009/0270764 A1 | 10/2009 | Buse et al. | |
| 2009/0321257 A1* | 12/2009 | Takahara | G01N 27/3272 |
| | | | 204/403.14 |
| 2010/0062520 A1* | 3/2010 | Lee | G01N 21/253 |
| | | | 435/287.1 |
| 2010/0168615 A1* | 7/2010 | Amano et al. | 600/583 |
| 2010/0286562 A1 | 11/2010 | Fujiwara et al. | |
| 2011/0053289 A1* | 3/2011 | Lowe et al. | 436/501 |
| 2012/0010486 A1* | 1/2012 | Fujiwara | A61B 5/1411 |
| | | | 600/345 |
| 2012/0010530 A1 | 1/2012 | Fujiwara et al. | |

FOREIGN PATENT DOCUMENTS

| | | |
|---|---|---|
| JP | 2004-529728 A | 9/2004 |
| JP | 2005-110712 A | 4/2005 |
| JP | 2006-314831 A | 11/2006 |
| JP | 2010-32501 A | 2/2010 |
| WO | 99/45375 A1 | 9/1999 |
| WO | 2005/057200 A1 | 6/2005 |
| WO | 2006/085876 A1 | 8/2006 |
| WO | 2007/088855 A1 | 8/2007 |

OTHER PUBLICATIONS

The Office Action; "Notice of Reason for Rejection," issued by the Japanese Patent Office on May 27, 2014, which corresponds to Japanese Patent Application No. 2010-243163 and is related to U.S. Appl. No. 13/284,071.

The extended European search report issued by the European Patent Office on Jul. 29, 2015, which corresponds to European Patent Application No. 11186872.5-1506 and is related to U.S. Appl. No. 13/284,071.

The partial European search report issued by the European Patent Office on Mar. 12, 2015, which corresponds to European Patent Application No. 11186872.5-1506 and is related to U.S. Appl. No. 13/284,071.

* cited by examiner

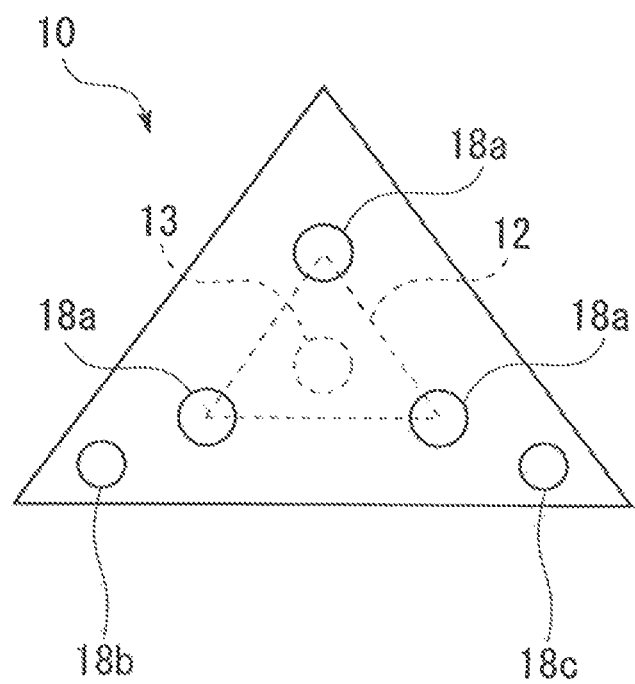

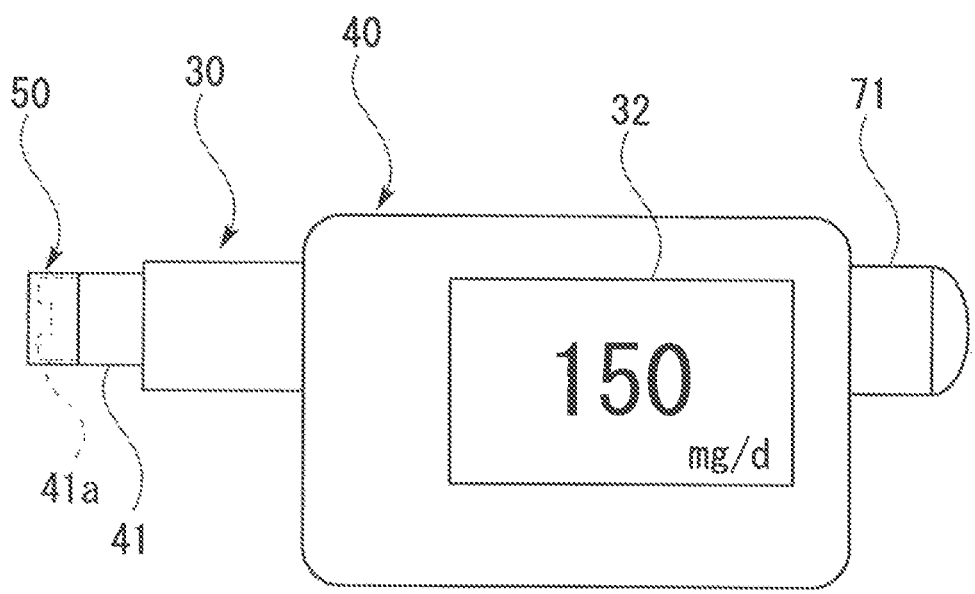

ELECTROCHEMICAL SENSOR, LANCET, AND BODILY FLUID MEASURING APPARATUS

CROSS-REFERENCE TO RELATED APPLICATION

This application claims the benefits of priority of the prior Japanese Patent Application No. 2010-243163 filed on Oct. 29, 2010, the entire contents of which are incorporated herein by reference.

FIELD

The present invention relates to an electrochemical sensor, a lancet and a bodily fluid measuring apparatus.

BACKGROUND

In the field of electrochemical sensors, there is a biosensor which uses enzymes for measuring the glucose concentration (glucose level) in the blood. For example, there is a biosensor configured by comprising a base plate in which a working electrode and a counter electrode are formed on an upper surface, a spacer which is superimposed on the base plate so as to form a groove facing a part of the working electrode and the counter electrode, respectively, a reactive site in which a reaction reagent layer is formed on a part or all of the groove, and a cover plate which is superimposed on the spacer, wherein a space that is surrounded by the groove and the cover plate forms the bodily fluid passage, and wherein a terminal part which is caused to conduct respective with the working electrode and the counter electrode and come in contact with a terminal of the body is disposed at an appropriate location on an upper surface of the base plate (for example, Patent document 1).

The biosensor described in Japanese Patent Application Laid-open No. 2006-314831 is integrally formed with a tool referred to as a lancet for opening a small hole (scratching) the skin; for instance, the fingertip, of a patient. A bodily fluid passage, in which the reactive site faces the inner surface thereof, is formed on the inside of the biosensor in the thickness direction thereof on the one hand, and a through-hole having a diameter that is larger than the puncture tool which is in communication with the bodily fluid passage and allows the passage of the tip of the puncture tool, and which penetrates the sensor in the thickness direction thereof and is opened to the lower surface of the sensor is also formed in the biosensor. Consequently, the blood that flows from the skin that was scratched by the puncture tool is introduced to the reactive site from the through-hole through the bodily fluid passage.

[Patent document 1] Japanese Patent Application Laid-open No. 2006-314831

SUMMARY

An object of aspects of the invention is to provide an electrochemical sensor that can be downsized.

The aspects of present invention adopts the following configurations in order to achieve the object.

Specifically, a first aspect of the present invention is an electrochemical sensor including: a base plate provided with a concave part formed on one of surfaces thereof, a fluid channel formed so that a bottom part of the concave part and the other one of the surfaces of the base plate are communicated with each other, a plurality of electrodes formed on the concave part, a reagent fixed on the electrodes, a cover which covers the concave part, and an air channel which causes the inside and outside of the concave part to be communicated with each other.

In the electrochemical sensor of the first aspect, an outer edge shape in planar view may be a triangle, a trapezoid, or a circle.

In the electrochemical sensor of the first aspect, the fluid channel can be a through-hole formed at the center of the concave part in planar view, and formed in a direction that is orthogonal to the base plate.

Moreover, in the electrochemical sensor of the first aspect, the air channel may include at least one air hole formed in the cover.

Moreover, in the electrochemical sensor of the first aspect, a planar view shape of the concave part may be formed in a triangle, and the air channel may include three air holes formed respectively at positions corresponding to apex portions of the triangle of the cover.

Moreover, in the electrochemical sensor of the first aspect, a planar view shape of the concave part may be formed in a circle, and the air channel may include an air hole formed on the cover and disposed so as to overlap with the through-hole in a planar view state of the base plate.

Moreover, the electrochemical sensor of the first aspect may further include a pair of second concave parts formed around the concave part, and the plurality of electrodes may include a first electrode pattern in which an electrode extending from the concave part to one of the pair of the second concave parts and an electrode removal part are formed integrally, and a second electrode pattern which is insulated from the first electrode pattern, and in which an electrode extending from the concave part to the other one of the second concave parts and an electrode removal part are formed integrally.

Moreover, with the electrochemical sensor of the first aspect, the other one of the surfaces of the base plate may be recessed inward.

A second aspect of the present invention is a lancet including: a lancet body, a mounting part which is provided to the lancet body and to which the electrochemical sensor according to the first aspect is mounted, with the one of surfaces facing the lancet body and the other one of the surfaces facing outward, and a puncture needle which can be freely advanced and retracted between a first position which is housed inside the lancet body and a second position which passes through the fluid channel of the electrochemical sensor mounted on the mounting part and protrudes from the other one of the surfaces.

In the lancet of the second aspect, negative pressure for causing a fluid to flow from the other one of the surfaces to the one of the surfaces may be applied to the fluid channel when a tip part of the puncture needle is retracted from the second position to the first position.

In the lancet of the second aspect, the electrochemical sensor may be mounted on the mounted part in a state of becoming integral with the lancet body.

Moreover, a third aspect of the present invention is a bodily fluid measuring apparatus which is able to be equipped with the lancet of the second aspect, including a plurality of terminals which come in contact with the respective electrodes of the electrochemical sensor of the first aspect mounted on the lancet, an electronic circuit which obtains a measurement signal via the plurality of terminals, and a drive mechanism which advances and retracts the puncture tool.

According to the present invention, the electrochemical sensor can be downsized.

BRIEF DESCRIPTION OF THE DRAWINGS

FIG. 6 is a diagram showing a modified example of the sensor;

FIG. 7 is a diagram showing an example of the bodily fluid measuring apparatus to which the sensor can be applied;

DESCRIPTION OF EMBODIMENTS

Embodiments of the present invention are now explained with reference to the appended drawings. The configurations of the embodiments are merely examples, and the present invention is not limited to the configurations of the embodiments.

<Electrochemical Sensor>

The electrochemical sensor according to an embodiment of the present invention is now explained. An electrochemical sensor is a sensor for detecting a specific test substance by using an electrochemical reaction, and a biosensor is applied in this embodiment. A biosensor is used for measuring and detecting a test substance by using a living substance or a material derived from a living substance as the element for detecting the test substance.

The electrochemical sensor in this embodiment is a biosensor that is used for measuring the glucose concentration (glucose level) in the blood, and is referred to as a glucose sensor. The electrochemical sensor is hereinafter simply referred to as the "sensor".

Figure 1A:
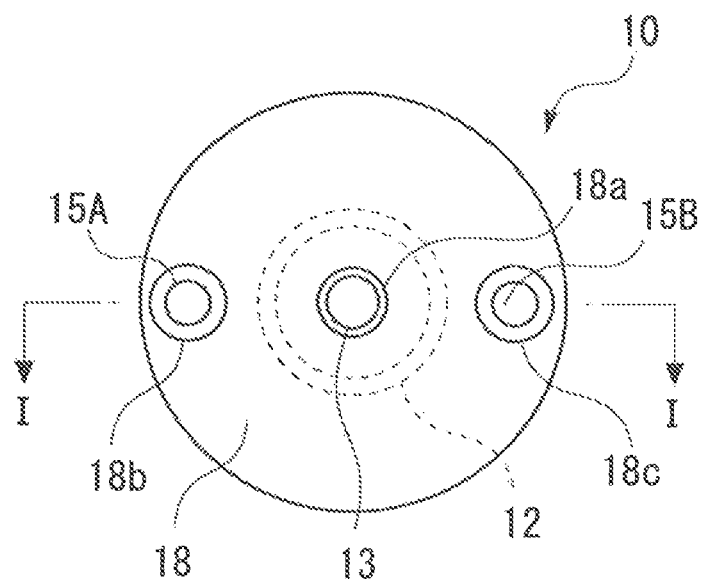
FIG. 1A is a plan view schematically showing a configuration example of the glucose sensor (electrochemical sensor) according to the first embodiment of the present invention.
Figure 1B:
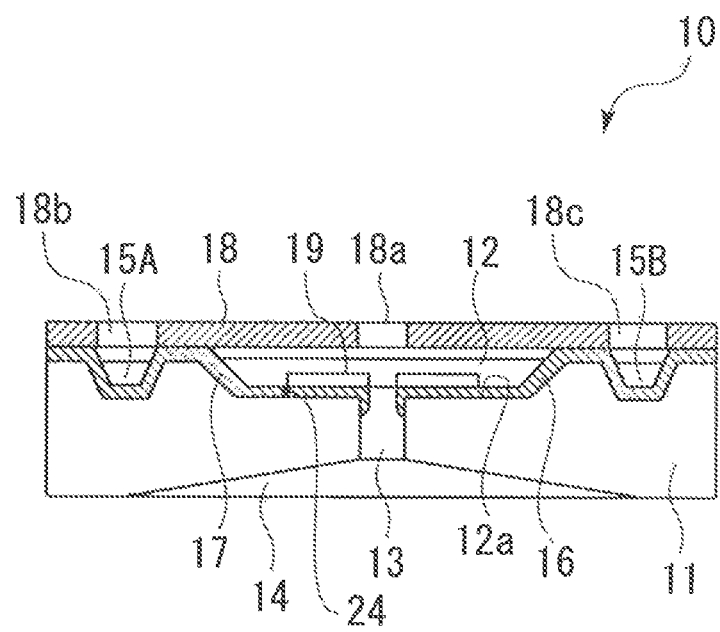
FIG. 1B is a diagram schematically showing a cross section of the glucose sensor illustrated in FIG. 1A by cutting it at line I-I in FIG. 1A.

FIG. 1A is a plan view schematically showing a configuration example of the electrochemical sensor according to the first embodiment of the present invention, and FIG. 1B is a diagram schematically showing a cross section of the glucose sensor illustrated in FIG. 1A by cutting it at line I-I in FIG. 1A.

In FIG. 1A and FIG. 1B, the sensor 10 as a whole is of a disk shape having a circular planar shape. The sensor 10 includes a disk-shaped base plate 11, and a concave part 12 having a flat circular shape is formed at the center of one surface (upper surface in FIG. 1B) of the base plate 11. The side wall of the concave part 12 is formed in a tapered shape where the diameter becomes smaller toward the bottom surface 12a of the concave part 12, and the surface shape of the concave part 12 is the inner periphery of a circular truncated cone in which the upper end thereof is opened. However, it is not an essential requirement for the side wall of the concave part 12 to be tapered, and the surface where the concave part 12 is formed can also be formed as a cylindrical inner surface in which the upper end thereof is opened.

A through-hole 13 for causing one surface and the other surface (lower surface in FIG. 1B) of the base plate 11 to be in communication is formed at the center of the concave part 12 (center in the diagram). The opening on the other surface side (lower surface side) of the through-hole 13 is in communication with a recess 14 formed on the lower surface. The recess 14 is formed as an inner peripheral shape of a substantial circular truncated cone in this embodiment. The recess 14 is formed so that the surface shape of the other surface of the sensor 10 conforms with the portion where the blood is to be collected (for example, ball of a finger).

Note that, in this embodiment, although the through-hole 13 is formed in a direction that is orthogonal to the planar direction of the base plate, it is not an essential requirement for it to be formed in an orthogonal direction, and it can also be formed obliquely. Moreover, the formation of the recess 14 is not an essential requirement.

Two second concave parts 15A, 15B are formed around the concave part 12. The second concave parts 15A, 15B have a circular planar shape of a diameter that is smaller than the inner diameter of the concave part 12, and, as with the concave part 12, is formed as inner periphery of a circular truncated cone having a tapered shape in which the upper end thereof is opened.

A metal layer configuring a plurality of electrodes that are used for measuring the glucose level is formed on the upper surface of the base plate 11. The plurality of electrodes comprises a counter electrode 17 that is formed integrally with the electrode lead line (lead part) from the bottom surface 12a of the concave part 12 to the second concave part 15A, and a working electrode 16 that is formed integrally with the electrode lead line (lead part) from the bottom surface 12a of the concave part 12 to the second concave part 15B (refer to FIG. 3A).

The working electrode 16 and the counter electrode are respectively connected to two external terminals which apply a voltage between the two electrodes and extract a response current. The external terminals are respectively inserted into the second concave parts 15A, 15B and respectively come in contact with the metal layer (working electrode 16, counter electrode 17), and become an electrically connected state. When, for example, a connector pin is used as the external terminal, and the respective connector pins are inserted to fit into the second concave parts 15A, 15B, and the connector pins may come in contact with the bottom surface of the second concave part 15A (15B) and the metal layer provided to the lateral surface thereof. Accordingly, since the contact area may be increased, a favorable contact state may be obtained in comparison to cases where the metal layer is a flat surface. Moreover, it is also possible to prevent the connector pin become shifted in the planar direction of the base plate 11. However, it is not an essential requirement to provide the second concave parts 15A, 15B.

Figure 3A:
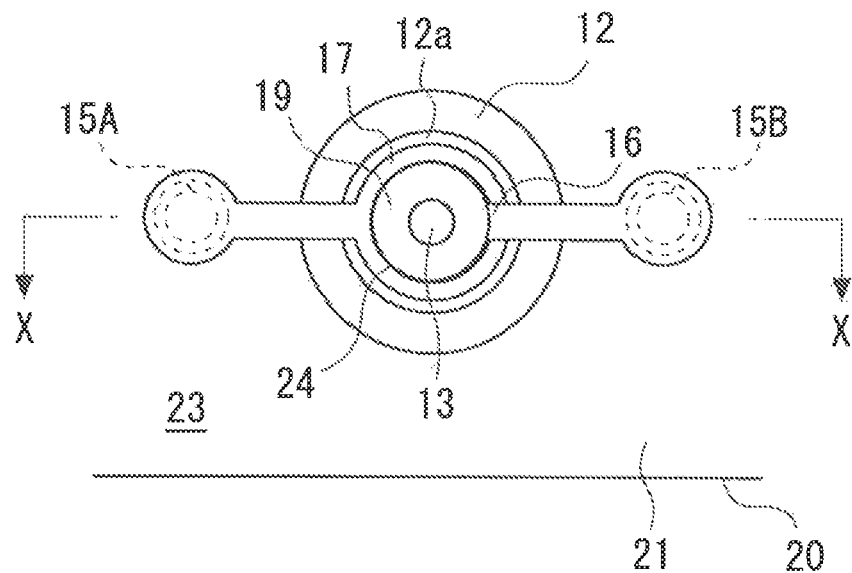
FIG. 3 is an explanatory diagram showing an example of the manufacturing method of the sensor.

The working electrode 16 is formed to surround the through-hole 13 and the counter electrode 17 is formed to surround the working electrode 16 on the bottom surface 12a of the concave part 12 (refer to FIG. 3A). A gap (groove 24, refer to FIG. 3A and FIG. 3B) is formed between the working electrode 16 and the counter electrode 17, and the electrodes are in an insulated state.

A reagent layer containing enzymes are immobilized on the electrodes. In the example shown in FIG. 1B, the reagent layer 19 containing enzymes are formed on the working electrode 16.

As the reactive agent configuring the reagent layer 19, for example, a type containing glucose oxidase (GOD) as an oxidizing enzyme and potassium ferricyanide as a mediator is used. When the reactive site is dissolved by blood, the potassium ferricyanide coexisting in the reagent layer is reduced due to the commencement of the well-known enzyme reaction, and potassium ferrocyanide as a reduction-type electron carrier is accumulated. The amount thereof is proportional to the substrate concentration; that is, the glucose concentration in the blood. The reduction-type electron carrier that has been accumulated for a given period of time is oxidized due to the electrochemical reaction caused by the application of voltage between the working electrode 16 and the counter electrode 17. The current referred to as the anode current (response current) that is generated here is extracted by the external terminal and measured by the measuring apparatus, and the measurement of the glucose level is thereby enabled.

Note that, as the enzymes for measuring the glucose level, glucose dehydrogenase (GDH) can be applied in addition to GOD. As the mediator upon applying GDH, for example, as with the case of GOD, potassium ferricyanide can be used.

Moreover, in this embodiment, although a glucose sensor is illustrated as an example of the electrochemical sensor, it is also possible to use cholesterol dehydrogenative enzymes (CHDH) as the enzymes contained in the reagent and use the sensor 10 as the biosensor (cholesterol sensor) for measuring the cholesterol.

The upper surface of the base plate 12 is covered by a cover 18 excluding a part of the concave part 12 and the second concave parts 15A, 15B. As a result of the concave part 12 being covered by the cover 18, the space surrounded by the concave part 12 and the cover 18 functions as a capillary, and the through-hole 13 functions as a fluid passage for introducing the bodily fluid (blood in this embodiment) flowing from the recess 14 side into the concave part 12 (capillary).

Accordingly, with the sensor 10 (electrochemical sensor) according to this embodiment, the fluid channel (through-hole 13) is formed in thickness direction of the base plate 11 just below the concave part 12 (capillary). Specifically, the sensor 10 comprises a through-hole 13 which functions as a fluid channel that causes the bottom surface of the concave part 12 and the other surface of the base plate 11 to be in communication. In addition, the blood is sucked from the other surface of the sensor 10 through the through-hole 13 based on the capillary phenomenon, and introduced into the concave part 12. Accordingly, the planar direction size of the base plate 11 can be reduced in comparison a case of forming the fluid channel in the planar direction of the base plate 11 as with the conventional technologies. Thus, the downsizing of the electrochemical sensor can be sought.

The cover 18 is formed with an opening 18a which functions as a capillary air hole (air channel) for causing the upper part of the concave part 12 to be in communication with the outside. In the example shown in FIG. 1A, the opening 18a is provided at the approximate center of the concave part 12, and, when the sensor 10 is seen from a planar view, the opening 18a and the through-hole 13 are formed so as to overlap. This overlap is not an essential requirement. It will suffice so as long as the opening 18a which functions as the air hole for causing the concave part 12 and the outside to be in communication is formed above the concave part. As described later, when a configuration where the puncture needle of the lancet passes through the through-hole 13 is adopted, the through-hole 13 and the opening 18a are configured to overlap.

Moreover, the cover 18 is formed with openings 18b, 18c on the second concave parts 15A, 15B for inserting the external terminals into the second concave parts 15A, 15B and causing the external terminals to come in contact with the electrodes (counter electrode 17, working electrode 16).

<Manufacturing Method of Sensor>

Figure 2A:
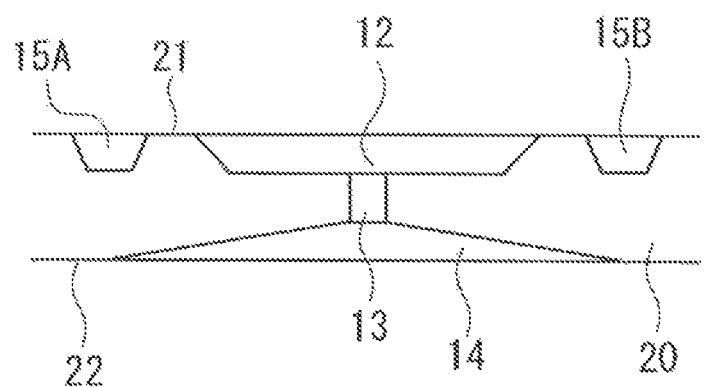
FIG. 2 is an explanatory diagram showing an example of the manufacturing method of the sensor.
Figure 2B:
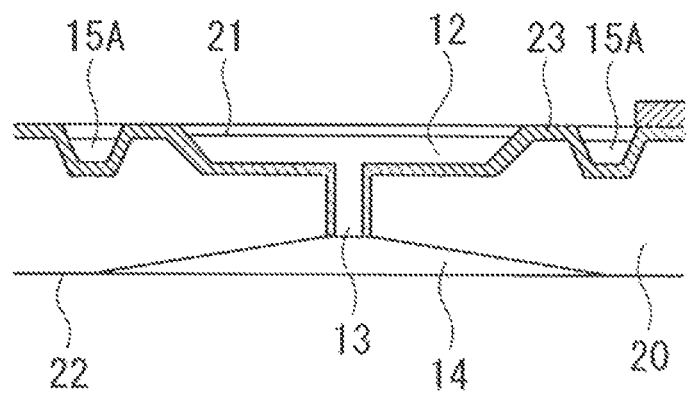
Figure 3B:
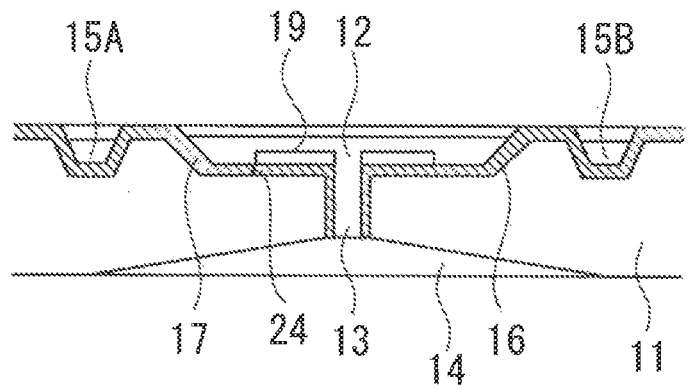
Figure 3C:
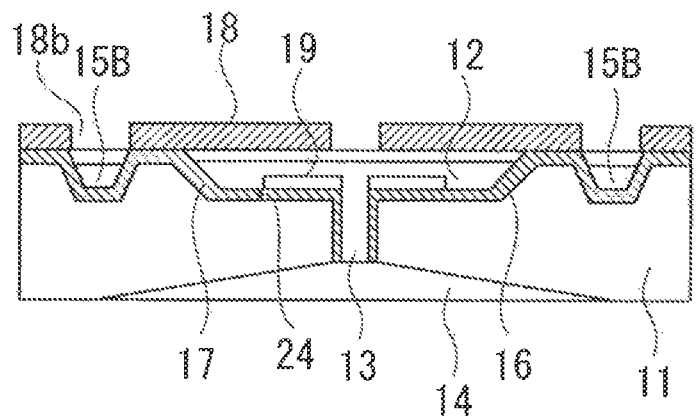

The manufacturing method of the foregoing sensor 10 is now explained. FIG. 2 and FIG. 3 are explanatory diagrams showing an example of the manufacturing method of the sensor. Note that, although FIG. 2 and FIG. 3 illustrate the manufacturing process of one sensor 10, in reality a plurality of sensors 10 are formed from one plastic base plate 20. Moreover, in relation to FIG. 2 and FIG. 3, the schematic view of the cross section shown in FIG. 2A and FIG. 2B and FIG. 3B and FIG. 3C shows the cross section upon cutting at line X-X illustrated in FIG. 3A.

A plastic base plate 20 to serve as the base plate 11 is foremost prepared, and, as shown in FIG. 2A, the concave part 12 and the second concave parts 15A, 15B formed on one surface 21 of the plastic base plate configuring the base plate 11 (refer to FIG. 3A), and the recess 14 is formed on the other surface 22. In addition, the through-hole 13 for causing the concave part 12 and the recess 14 to be in communication in the thickness direction of the base plate 20 is formed.

The plastic base plate 20 can be formed from thermoplastic resin, polyimide resin or epoxy resin such as polyethylene terephthalate (PET), polypropylene (PP), polyethylene (PE), and polycarbonate that is harmless to the human body and which as appropriate insulation properties and elasticity.

The concave part 12, the second concave parts 15A, 15B, the recess 14, and the through-hole 13 can be formed via various plastic molding methods such as the compression method, the transfer method, or the injection method. When using the plastic molding method, the concave part 12, the second concave parts 15A, 15B, the recess 14, and the through-hole 13 can be temporarily formed via the molding process.

Needless to say, the concave part 12, the second concave parts 15A, 15B, the recess 14, and the through-hole 13 can be formed on the base plate 20 via laser irradiation or the machining process. In the foregoing case, with the example shown in FIG. 2A, the order of forming the concave part 12, the second concave parts 15A, 15B, the recess 14, and the through-hole 13 can be set suitably, and they do not need to be collectively formed at once.

Next, as shown in FIG. 2B, the metal layer 23 is formed on one surface of the plastic base plate 20. The metal layer 23 can be formed, for example, by subjecting metal such as gold or platinum to physical vapor deposition (PVD; sputtering for instance), or chemical vapor deposition (CVD).

Next, a plurality of electrodes are formed on one surface 21. FIG. 3A shows the planar view of the base plate 20 in a state where the metal layer 23 is formed, and a state where the working electrode 16 and the counter electrode 17 are formed. As shown in FIG. 3A, as a result of trimming the metal layer 23 formed on the one surface 21 by using a laser, the working electrode 16 and the counter electrode 17 are formed.

Specifically, the working electrode 16 is formed by performing laser irradiation so as to form an electrode pattern (first electrode pattern) of the working electrode 16 containing an electrode lead line from the concave part 12 to the second concave part 15B. Moreover, the counter electrode 17 is formed by performing laser irradiation so as to form an electrode pattern (second electrode pattern) of the counter electrode 17 containing an electrode lead line from the concave part 12 to the second concave part 15A.

With the portion that was irradiated by the laser, the metal layer is removed and a groove 24 is thereby formed. Consequently, the opposing metal layers become an insulated state with the laser-irradiated portion as the boundary. Thus, in the concave part 12, the working electrode 16 and the counter electrode 17 become an insulated state across the groove 24 (refer to FIG. 3A and FIG. 3B) that was formed by removing the metal layer via laser irradiation. Thus, when laser trimming is applied for forming the electrodes, the side wall of the concave part 12 is preferably formed in a tapered shape in which the diameter becomes smaller toward the bottom surface (for example, the cross section shape of the concave part 12 is a trapezoid where the base is shorter than the top edge) so as to form an appropriate groove 24 on the side wall of the concave part 12.

Next, the reagent layer 19 is formed (immobilized) on the working electrode 16. The reagent layer 19 can be formed, for example, via the divided injection method. Subsequently, the one surface 21 of the plastic base plate 20 is covered by the cover 18. The cover 18 can be mounted, for example, by using a sheet-shaped PET and disposing it on the one surface 21 and performing thermal fusion bonding thereto. As the cover 18, a cover material in which openings 18a, 18b, 18c are formed in advance can also be used, or the openings 18a, 18b, 18c can be formed after the cover material is mounted (after the thermal fusion bonding).

Then, as a result of cutting the plastic base plate 20, a plurality of sensors 10 are cut out from the plastic base plate 20.

Modified Example

In the example illustrated in FIG. 1A, the planar shape of the sensor 10 was a circle, but the planar shape can also be polygonal including a triangle or a rectangle, or oval. Needless to say, the planar shape of the sensor 10 can also be a triangle as shown in FIG. 4 or a trapezoid as shown in FIG. 5.

When the planar shape is formed in a triangle, the number of sensors 10 that can be obtained from one plastic base plate 20 can be increased in comparison to the case of forming the planar shape in another shape. From the perspective of increasing the number of sensors to be obtained from one plastic base plate 20, the triangle is preferably an equilateral triangle. Moreover, the same effect can be yielded when the planar shape of the sensor 10 is formed in the shape of an isosceles trapezoid where one apex of the triangle is cut off. The direction of the sensor 10 can be decided easily by forming the planar shape of the sensor 10 as a trapezoid.

Figure 4:
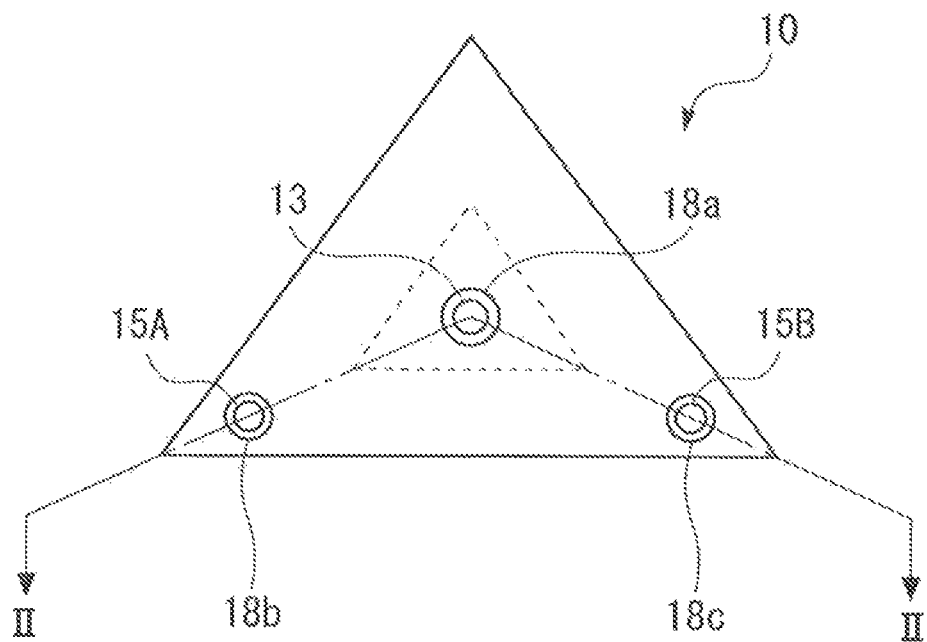
FIG. 4 is a diagram showing a modified example of the sensor.
Figure 5:
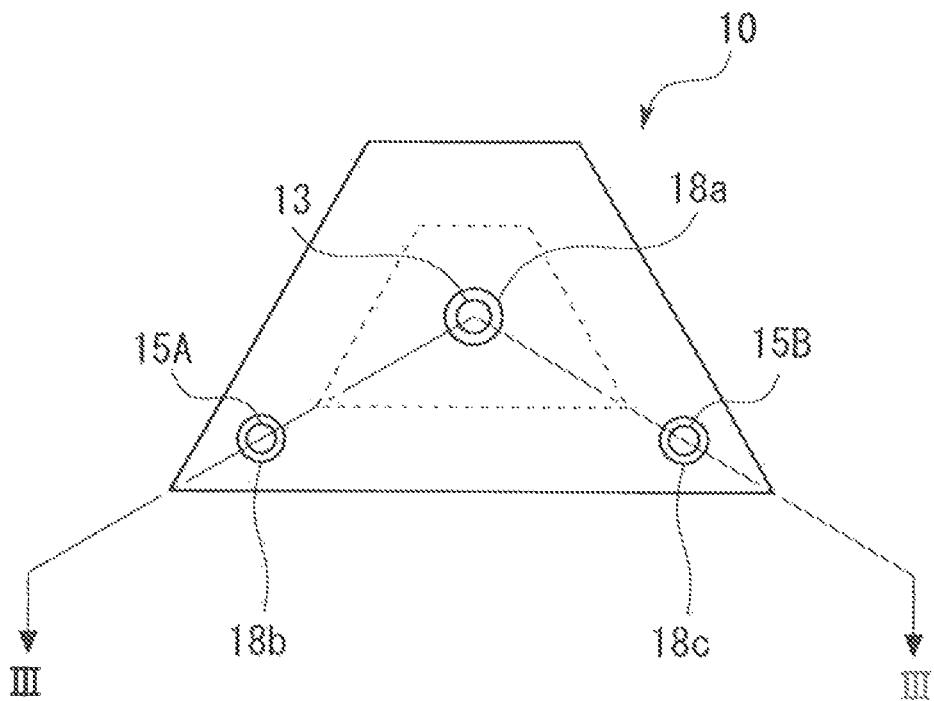
FIG. 5 is a diagram showing a modified example of the sensor.

When the planar shape of the sensor 10 is formed in a triangle or a trapezoid, as shown in FIG. 4 and FIG. 5, the second concave parts 15A, 15B are not disposed linearly relative to the concave part 12 as shown in FIG. 1, but are rather disposed, for example, on the straight line that connects the center of the triangle or the trapezoid, and the respective apexes which are formed by the base of the triangle or the trapezoid and the other sides. In the foregoing case, the cross section upon cutting the sensor at line II-II of FIG. 4 and the cross section upon cutting the sensor 10 at line III-III of FIG. 5 will be the same as the structure shown in FIG. 1B. Needless to say, the position of the second concave parts 15A, 15B relative to the concave part 12 can be suitably set. Moreover, the planar shape of the second concave parts 15A, 15B can also be suitably set.

Moreover, although the planar shape of the concave part 12 was a circle in the example shown in FIG. 1A, preferably, the concave part 12 is formed in a triangle with the sensor 10 in which the planar shape is a triangle as shown in FIG. 4, and formed in a trapezoid with the sensor 10 in which the planar shape is a trapezoid as shown in FIG. 5. As described above, when the planar shape of the concave part 12 is formed in the same shape (particularly a similar figure) as the planar shape of the sensor 10, this is preferable from the perspective that the capacity of the capillary that is formed by the concave part 12 can be maximized.

Moreover, when the planar shape of the concave part 12 is a triangle, preferably, while the through-hole 13 is positioned at the center of the triangle, the three openings 18a are disposed so as to overlap with the respective apexes of the triangle of the concave part 12. Consequently, these will be disposed at positions where the distance between the inlet (upper end of the through-hole 13) of the blood provided at the center of the concave part 12 and the respective air holes (respective openings 18a) becomes the greatest, and the blood that flows from the center of the concave part 12 through the through-hole 13 will spread evenly in the concave part 12. Thus, the time required for the blood to reach the air hole (opening 18a) and air bubbles to be eliminated can be prolonged.

Moreover, in the example of the sensor 10 according to this embodiment described above, a case where the reagent layer 19 is formed on the working electrode 16 was explained. However, the reagent can also be disposed across the working electrode 16 and the counter electrode 17. The reagent layer 19 preferably covers the overall upper surface of the working electrode 16, but when it is placed across the counter electrode 17, it will suffice if a part of the counter electrode 17 is covered.

<Bodily Fluid Measuring Apparatus and Lancet>

Figure 8A:
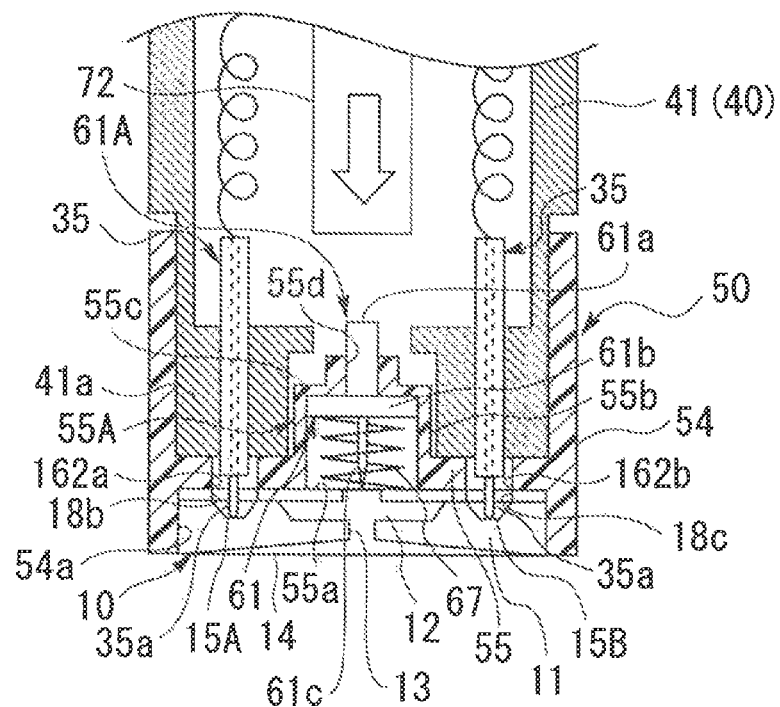
FIG. 8A and FIG. 8B are diagrams showing a cross section configuration example of the mounted body that is mounted on the body of the bodily fluid measuring apparatus.
Figure 8B:
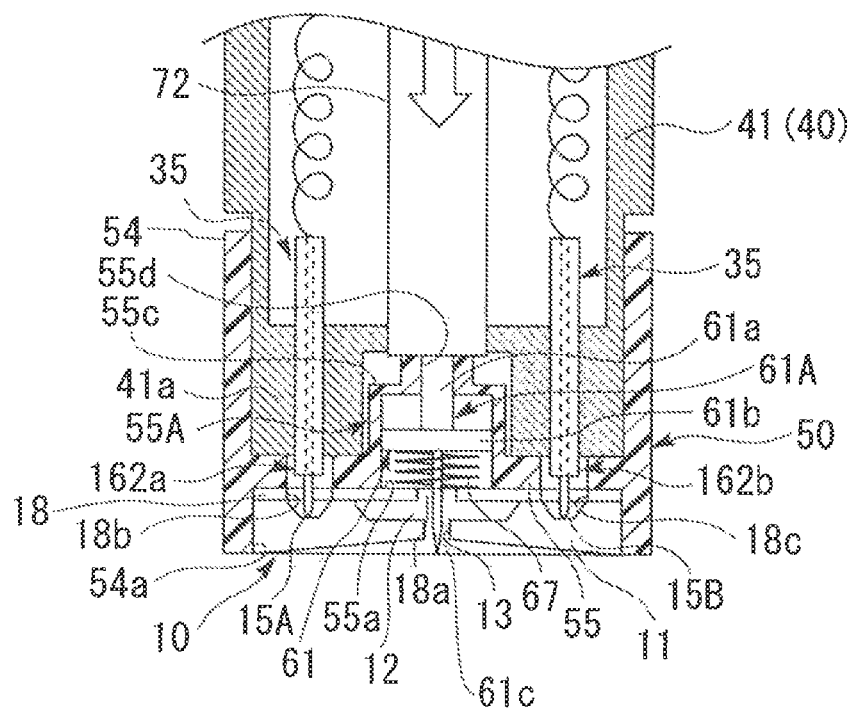
Figure 9A:
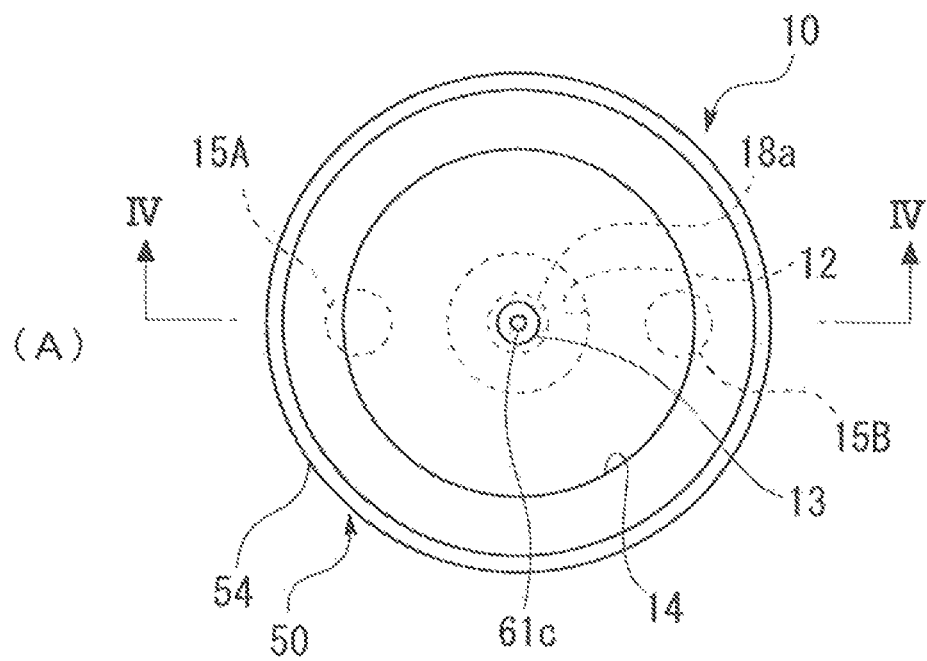
FIG. 9A is a diagram showing the tip surface of the mounted body that is mounted on the sensor in a planar view.
Figure 9B:
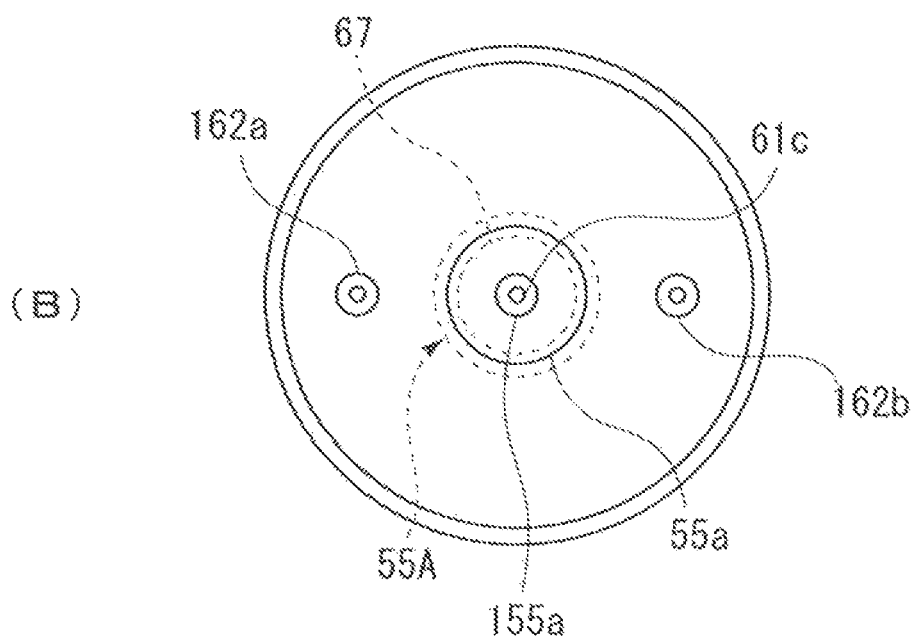
FIG. 9B is a diagram showing a state where the sensor is removed.

The bodily fluid measuring apparatus to which the foregoing sensor 10 is applied and the lancet are now explained. FIG. 7 is an overall external view of the bodily fluid measuring apparatus according to this embodiment, and FIG. 8A is an enlarged longitudinal cross section showing the details of the mounted body in a state where the puncture tool is retracted and is a diagram corresponding to the cross section along line IV-IV of FIG. 4. FIG. 8B is an enlarged longitudinal cross section showing the details of the mounted body in a state where the puncture tool is advanced. FIG. 9A is a bottom surface view of the mounted body, and FIG. 9B is a bottom surface view of the mounted body in a state where the sensor is removed.

As shown in FIG. 7 to FIG. 9, the bodily fluid measuring apparatus 30 is used by combining the body 40 and the mounted body 50 (corresponds to the lancet body). The body 40 has switch buttons (not shown) and an LCD display device 32 disposed on its upper surface. A tubular part 41 is formed in a protruding manner at the front part of the body 40, and a cap-shaped mounted body 50 described later is mounted on the tip part of the tubular part 41.

A drive mechanism (71, 72) for forward-driving the puncture tool 61 of the mounted body 50 and an electronic circuit of a microcomputer or the like are built into the body 40. The drive mechanism is provided at the rear of the body 30 in FIG. 1, and includes a pressing part 71 to be manually pressed by the user.

A configuration example of the mounted body 50 is now explained with reference to FIG. 8A, FIG. 8B, FIG. 9A and FIG. 9B. The mounted body 50 is formed in a substantial cap shape comprising a cylindrical part 54, and a bottom wall part 55 positioned so as to cover the tip of the cylindrical part 54 in the cylindrical part 54. The main parts of the cylindrical part 54 and the bottom wall part 55 can be prepared by resin molding.

The end part 41a of the tubular part 41 of the body 40 is formed to have a diameter that is smaller than the base end part of the tubular part 41, and the inner diameter of the cylindrical part 54 corresponds to the outer diameter of the end part 41a of the tubular part 41, and the mounted body 50 is fitted and fixed to the end part 41a by covering the end part 41a. Accordingly, the mounted body 50 can be easily mounted removably to a predetermined location of the body 40 (end part 41a of the tubular part 41). The outer surface of the bottom wall part 55 functions as the mounting surface for mounting the sensor 10 described above (refer to FIG. 1).

A puncture tool 61 is mounted on the bottom wall part 55 of the mounted body 50. In addition, the side face of the sensor 10 is fitted into the inner circumferential wall 54a of the cylindrical part 54, the upper surface of the sensor 10 comes in contact with the lower surface of the bottom wall part 55, and the sensor 10 is thereby mounted on the mounted body 50. A cylindrical housing part 55A having a discoid wall 55a, a cylindrical wall 55b, and a bottom wall 55c with an opening 155a (refer to FIG. 9B) at the center is formed at the center position of the mounted body 50 at the bottom wall part 55, and a center hole 55d is opened at the bottom wall 55c of the housing part 55A.

The puncture tool 61 is configured by a metal puncture needle 61c being mounted coaxially and integrally on a resin guide body 61A having a guide shaft 61a which slidably fits with the center hole 55d, and a flange part 61b which is formed integrally with one end of the guide shaft 61a.

In the housing part 55A, an elastic body 67 is interposed between the lower surface of the flange part 61b and the upper surface of the cylindrical wall 55a. In the case shown in FIG. 8A and FIG. 8B, the elastic body 67 is a coil spring that presses (biases) the flange part 61b in a direction of being separated from the discoid wall 55a. Needless to say, in substitute for the coil spring, urethane foam can also be used. Otherwise, the elastic body 37 can also be a plate-shaped spring that is integrally formed with a resin guide body 61A.

Based on the elastic body 67, the flange part 61b is biased toward the retract position (first position) shown in FIG. 8A; that is, toward the position in which the flange part 61b comes in contact with the bottom wall 55c. In the retract position, the rear end (upper end) of the guide shaft 61a will protrude from the housing part 55A, and the tip part of the puncture needle 61c will retract inside the housing part 55A.

As described above, the sensor 10 is mounted on the mounted body 50 so as to cover the housing part 55A housing the puncture tool 61. A case where the sensor 10 is fitted inside the cylindrical part 54 was explained above, but the sensor 10 can also be attached to the bottom wall part 55.

The sensor 10 is mounted in a state where one surface (upper surface) faces the bottom wall part 55 and the planar direction of the sensor 10 is orthogonal to the center axis of the cylindrical part 54. In this mounted state, the opening 18a (air hole) of the sensor 10 and the through-hole 13 (fluid channel) are disposes substantially coaxial with the puncture needle 61c in the axis direction of the cylindrical part 54 (FIG. 9A).

As shown in FIG. 8A and FIG. 8B, as well as FIG. 9A and FIG. 9B, round holes 162a, 162b are formed on the bottom wall part 55 of the mounted body 50 at positions corresponding to the second concave parts 15A, 15B of the sensor 10.

The round hole 162b is used for causing one tip of the connector pins 35a provided inside the body 20 to come in contact with the electrode lead line of the metal layer; that is, the working electrode 16, formed on the second concave part 15B when the mounted body 50 is mounted on the body 30 (tubular body 40). Meanwhile, the round hole 162a is used for causing the other tip of the connector pins 35a provided inside the body 20 to come in contact with the electrode lead line of the metal layer; that is, the counter electrode 17, formed on the second concave part 15A when the mounted body 50 is mounted on the body 30 (tubular body 40).

Meanwhile, a pair of pin connectors 35 is disposed in parallel in the tubular part 41 of the body 30 in its axis direction, and configured such that the connector pins 35a elastically protrude from the tip part of the pin connectors 35. One connector pin 35a passes through the round hole 162a and the opening 18c of the sensor 10 and is inserted into the second concave part 15B, and comes in contact with the electrode lead line of the working electrode 16. The other connector pin 35a passes through the round hole 162b and the opening 18b of the sensor 10 and is inserted into the second concave part 15A, and comes in contact with the electrode lead line of the counter electrode 17.

Figure 10:
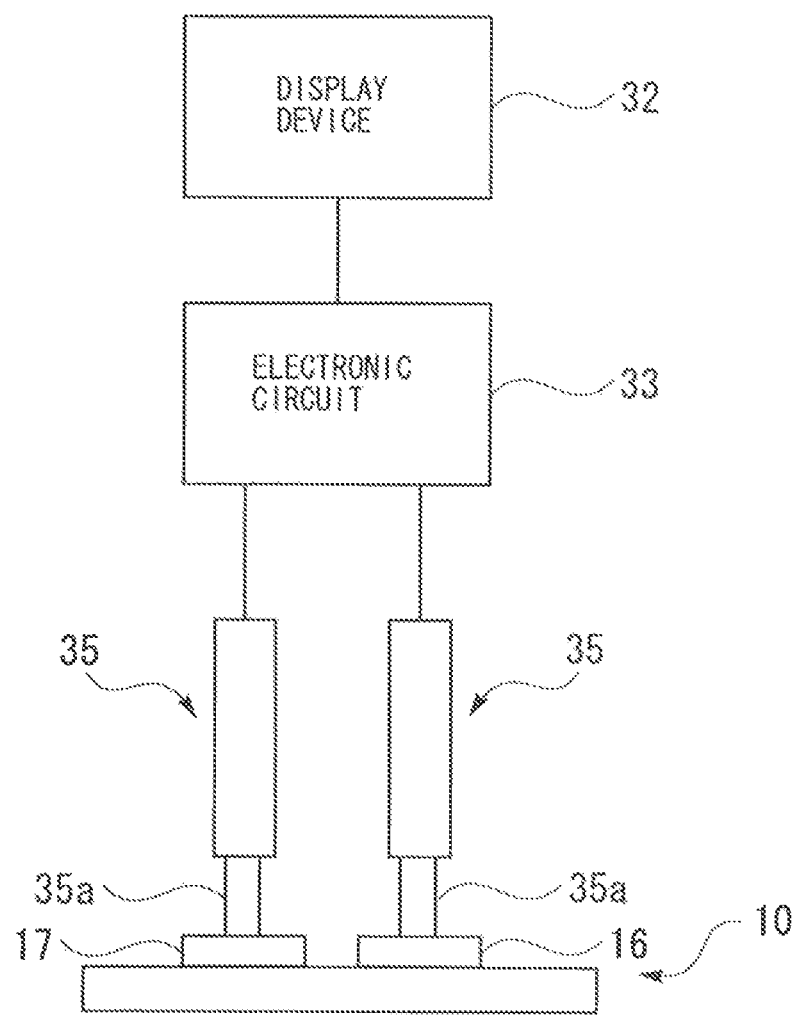
FIG. 10 is a diagram showing the electrical configuration of the sensor and the measuring apparatus.

The pin connectors 35 are connected to the electronic circuit 33 as shown in FIG. 10. The electronic circuit 33 is configured from a microcomputer, a memory and the like, and, by the microcomputer executing a program stored in the memory, it functions to determine the measured value of the specimen such as its glucose level by using the standard curve from the enzyme reaction and electrochemical reaction that occur in the capillary of the sensor 10 as described later, and display the measured value on a display device 32 disposed on the surface of the body 40.

Moreover, a pressing rod 72 for causing the inside of the tubular part 41 of the body 40 to retreat in the axis direction of the tubular part 41 according to the pressing operation of the pressing part 71 shown in FIG. 7 is disposed in the body 40. The pressing rod 72 is biased toward the pressing part 71 side (rearward side) by a spring not shown. The drive mechanism including the pressing part 71 and the pressing rod 72 is configured as described above. Consequently, when the pressing part 71 is pressed, the pressing rod 72 moves toward the front side (tip side) against the biasing force of the spring, comes in contact with the rear end part of the guide shaft 61a, and thereby presses the puncture tool 61A forward.

The tip part of the puncture needle 61c of the puncture tool 61A thereby passes through the opening 18a of the sensor 10 and the through-hole 13 and moves to the second position which protrudes outward from the lower surface of the sensor 10. Thus, the outer diameter of the puncture needle 61c is formed to be a smaller diameter than the inner diameter of the through-hole 13.

The inside of the housing part 55A is of a state where the side face of the flange part 61b and the inner peripheral surface of the cylindrical wall 55b are in contact, and, when the flange part 61b advances forward (downward) from the retract position, the air in the housing part 55A will be discharged to the outside through the through-hole 13 if the through-hole 13 is not covered. Meanwhile, even if the lower end of the through-hole 13 is covered by skin or the like, the flange part 61b as a result of the air inside the housing part 55A being compressed. In the foregoing case, when the pressing rod 72 retreats and the flange part 61b is pressed backward (upward) by the biasing force of the elastic body 67, negative pressure is generated inside the housing part 55A. This negative pressure induces the effect of causing the fluid existing in the recess 14 of the sensor 10 to be drawn into the concave part 12 (capillary) via the through-hole 13. Accordingly, when the puncture needle 61c is retreated, the fluid (blood) existing in the recess 14 will be introduced into the concave part 12 through the through-hole 13 (fluid channel) based on the negative pressure that was generated in the housing part 55A, in addition to the capillary action.

Note that, as the drive mechanism, without limitation to the illustrated example, it is also possible to adopt a configuration of providing a pressing rod 72 capable of moving in the axis direction and which will elastically return to the neutral position in the axis direction, bending the pressing rod 72 backward to retain the latch, pressing the latch release button so that the pressing rod 72 advance forward forcefully, the pressing rod 72 forcefully hammering the rear end of the guide shaft 61a of the puncture tool 61, and thereby causing the puncture needle 61c to instantaneously protrude from the other surface (lower surface) of the sensor 10.

Moreover, as the terminal (external terminal) that is provided inside the body 40 so as to enable conductive conduct with the terminal parts of the sensor 10 (respective electrode lead lines of the working electrode 16 and the counter electrode 17) when the mounted body 50 is mounted on the body 40, in addition to applying the pin connector 35 in which the pin is constantly protruding elastically as described above, for example, it is also possible to adopt a configuration where, in coordination with the mounting of the mounted body 50 on the body 40, the terminal pin is retreated inside the body when the mounted body 50 is not mounted, and appropriate conductive conduct is sought with the terminal part of the biosensor as a result of the terminal pin protruding from the body when the mounted body 50 is mounted.

The method of use and operation of the bodily fluid measuring apparatus 30 comprising the foregoing configuration are now explained with reference to FIG. 7 to FIG. 10.

The mounted body 50; that is, the lancet with the built-in sensor is provided as a disposable consumable supply, and, upon using the bodily fluid measuring apparatus 30, the user mounts the mounted body 50 on the tubular part 41 of the body 40 (refer to FIG. 7).

Since the mounted body 50 is formed in a cap shape, the foregoing mounting process can be performed easily. When the mounted body 50 is mounted, as shown in FIG. 8A, the tip of the connector pins 35a housed in the body 40 automatically comes in contact with the second concave parts 15A, 15B via the round holes 162a, 162b of the bottom wall part 55 of the mounted body 50 and the openings 18b, 18c of the sensor 10. Consequently, the counter electrode and the working electrode 16 become electrically connected with the measuring apparatus 30.

The tip of the mounted body 50; that is, the lower surface of the sensor 10 is pressed against an appropriate location of the skin of the user or the patient; for example, the fingertip or earlobe. Here, since the recess 14 is formed on the lower surface of the sensor 10, the lower surface of the sensor 10 can be caused to come in contact with the skin in a favorable state.

In the foregoing state, when the pressing part 71 (FIG. 7) is pressed downward, based on the stroke where the tip of the pressing rod 72 housed inside the body 40 presses the rear end part of the guide shaft 61a of the puncture tool 61, and the tip of the pressing rod 72 comes in contact with the housing part 55A, the puncture tool 61 at the retract position (first position) is pressed forward against the elastic force (biasing force) of the elastic body 67.

Here, the puncture needle 61c of the puncture tool 61 passes through the opening 18a, the concave part 12, and the through-hole 13 of the sensor 10 and protrudes from the lower surface of the sensor 10 a predetermined length (advances to the second position (advance position); refer to FIG. 8B). When the pressing to the pressing part 71 is released, the pressing rod 72 returns to its original position based on the elastic force of a spring not shown. Moreover, the puncture tool 61 also returns to the retract position (first position) where the tip of the puncture needle 61c enters the housing part 55A based on the elastic force of the elastic body 67 (refer to FIG. 8A).

Due to the protrusion of the puncture needle 61c, the skin is scratched appropriate, and the blood flowing from the scratch is introduced into the concave part 12; that is, the capillary, via the through-hole 13 due to the negative pressure that is generated within the housing part 55A based on the capillary phenomenon and the retreat of the puncture tool 61. Specifically, since the blood will be introduced into the capillary, which is the target position, if it flows a distance of the length of, or a distance that is slightly longer than, the through-hole 13, the capillary can be filled with blood with a small amount of blood and in a short period of time.

Accordingly, the user can introduce sufficient blood, which is required for measurement, into the capillary (concave part 12) of the sensor 10 by performing the pressing operation in a state of pressing the sensor 10 against the skin without having to visually confirm the amount of blood of the bleeding part, and then maintaining the state after releasing the pressing force.

In the concave part 12, when the reagent layer 19 is dissolved by the blood, the potassium ferricyanide that coexists in the reagent layer 19 is reduced due to the commencement of the enzyme reaction of the enzymes (GOD) contained in the reagent layer 19, and potassium ferrocyanide as a reduction-type electron carrier is accumulated.

The cumulative dosage of the potassium ferrocyanide is proportional to the substrate concentration; that is, the glucose concentration in the blood. The reduction-type electron carrier that has been accumulated for a given period of time is oxidized due to the electrochemical reaction caused by the application of voltage between the working electrode 16 and the counter electrode 17.

The electronic circuit 43 in the body 40 of the measuring apparatus 30 computes and determines the glucose concentration (glucose level) from the working current (response current) that is measured via the pin connectors 35, and displays the results on the display device 32.

Thus, according to the bodily fluid measuring apparatus 30, measurement of a bodily fluid such as the glucose level can be appropriately performed only based on an operation of causing the puncture needle 61c to protrude as though handling a conventional lancet while retaining the sensor 10 mounted on the front surface of the mounted body 50 in a state of being pressed against the fingertip or earlobe of the patient, after a simple preliminary preparation of mounting the mounted body 50 on a predetermined location of the body 40, without requiring any additional operation or movement. Moreover, after use, the mounted body 50 can be disposed without touching the blood merely by holding the side surfaces of the mounted body 50 and removing it from the body 40 and disposing the same.

Note that, in the example shown in FIG. 7 to FIG. 10, a case where the sensor 10 is formed integrally with the mounted body 50 as the lancet was explained. Needless to say, the sensor 10 shown in this embodiment can also be used independently; that is, by pinching the sensor 10 with fingers or the like and pressing the lower surface of the sensor 10 to the blood flowing from the skin using a lancet or the like, the capillary can be filled with the blood, and the sensor 10 can be subsequently set on the measuring apparatus in order to measure the blood.

Figure 11A:
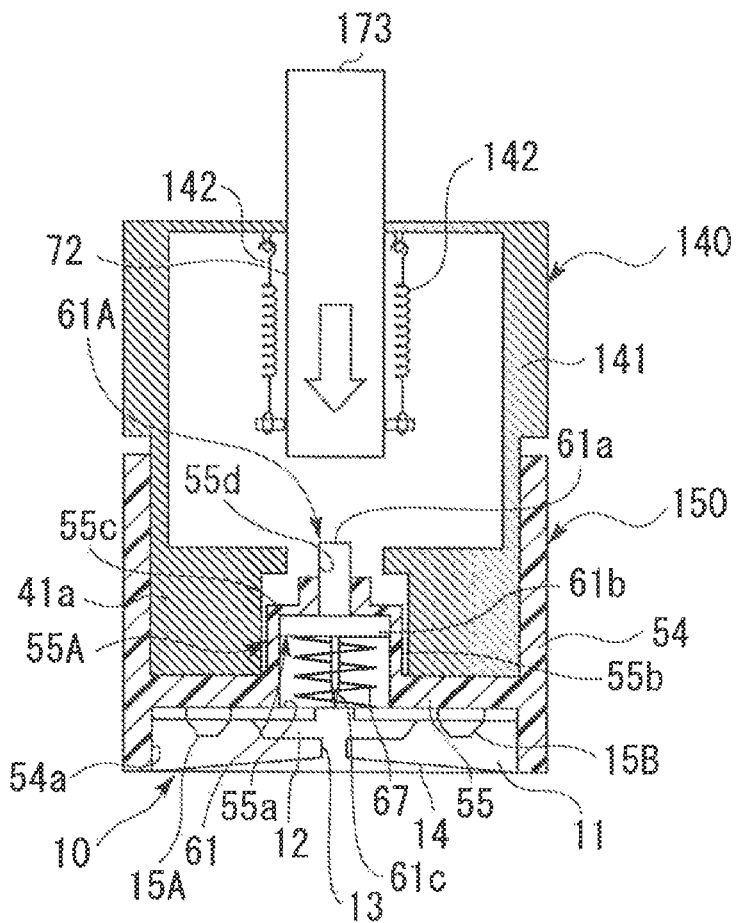
FIG. 11A and FIG. 11B are diagrams showing an example of the lancet with a built-in sensor without the measurement function.
Figure 11B:
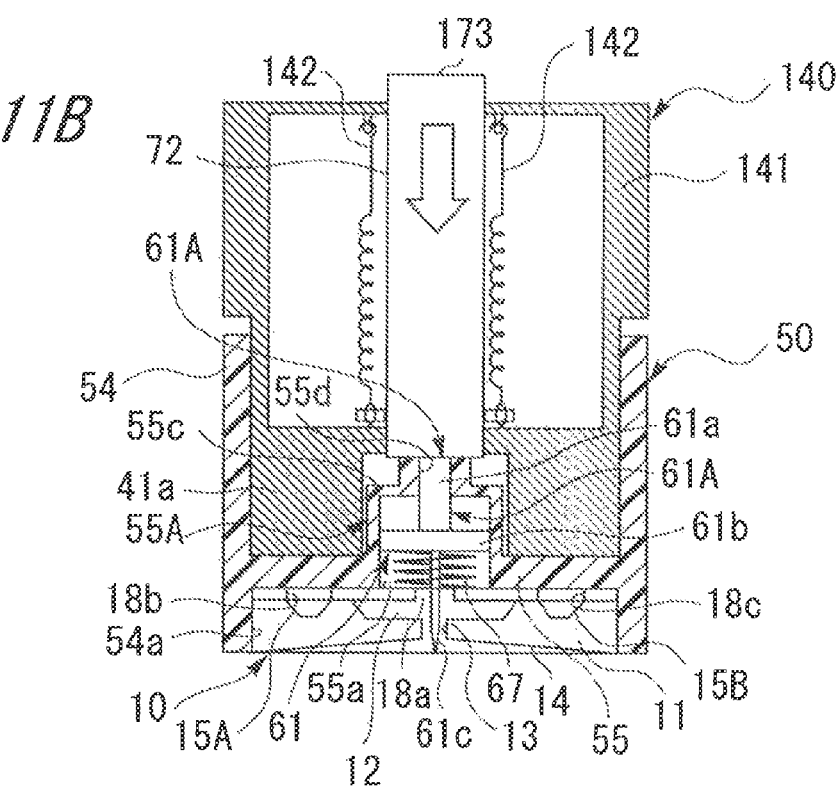

Moreover, as shown in FIG. 11A and FIG. 11B, the sensor 10 can also be applied to the lancet 140 to which the foregoing mounted body 50 is mounted. In the example shown in FIG. 11A and FIG. 11B, the lancet 140 is not provided with components (pin connector 35) for enabling the electrical connection with the sensor 10, and the pressing part 173 that is formed integrally with the pressing rod 72 is caused to protrude rearward of the body 141 by the tension springs 142 provided inside the body 141. With this kind of lancet 140, by pressing the pressing part 173, it is possible to cause the puncture needle 61c to protrude from the lower surface of the sensor 10, and fill the concave part 12 with blood.

Figure 12:
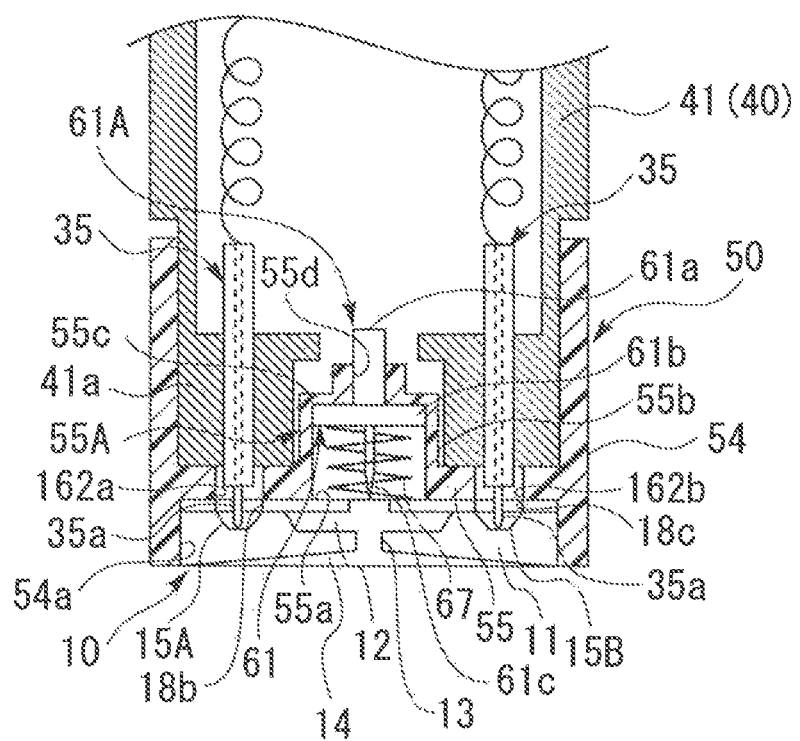
FIG. 12 is a diagram showing a configuration example of the measuring apparatus without the puncture function.

Subsequently, the mounted body 50 is dismounted from the body 141, and the mounted body 50 is mounted on the end part 41a of the tubular part 41 of the body 40 as shown in FIG. 12. The pressing rod 72 is not provided inside the body 41 shown in FIG. 12. Moreover, although not shown, the pressing part 71 is omitted from the external view of the measuring apparatus 30 shown in FIG. 7. Meanwhile, the pin connectors 35 are housed inside the body shown in FIG. 12, and, as with the similar effect described above, the connector pins 35a automatically come in contact with the working electrode 16 and the counter electrode 17, and the sensor 10 and the measuring apparatus 30 become electrically connected.

Otherwise, in substitute for the configuration of the lancet 140 shown in FIG. 11; that is, in substitute for the body 141 and the mounted body 50 being formed integrally, the sensor 10 can be removably attached to the lancet, and the sensor 10 in which the capillary (concave part 12) is filled with blood can be set in the measuring apparatus (not shown). Here, a chuck mechanism can be provided to the tip part lancet so that the sensor 10 is retained by the chuck mechanism.

Note that, in the configuration example of the lancet (mounted body 50, lancet 140) of the embodiment described above, a case where the sensor 10 in which air holes (openings 18a) are formed in advance is mounted on the lancet was explained. Needless to say, with the configuration of the lance of this embodiment, since the puncture needle 61c passes through the cover 18 of the sensor 10 since the puncture needle 61c passes through the through-hole 13, the air holes can be consequently formed on the cover 18. Thus, it is also possible not to form the air holes in advance.

Moreover, it is also possible to adopt a configuration where a separate needle, which coordinates with the puncture needle and has a diameter that is larger than the puncture needle, is provided inside the lancet, the separate needle also advance according to the advancement of the puncture needle, and the air holes are formed at the appropriate positions on the cover.

Needless to say, from the perspective of reliability of the air holes that are formed by the puncture needle 61c and the separate needle, it is preferable to form in advance the openings 18a (air holes) having an inner diameter that is larger than the outer diameter of the puncture needle 61c.

Moreover, in the example shown in FIG. 7 to FIG. 12, the sensor 10 in which its planar shape is a circle was illustrated, but the bodily fluid measuring apparatus 30 (mounted body 50, body 40) and the lancet 140 of this embodiment can be applied irrespective of the planar shape of the sensor 10. For example, the sensor 10 as shown in FIGS. 4 to 6 can be applied. However, the shape of the mounting part of the sensor 10 in the mounted body 50 is modified so that it can retain the sensor 10 (for instance, so that the sensor 10 can be fitted therein) according to the planar shape of the sensor 10. Moreover, the position of the pin connectors 35 and the round holes 162a, 162b is changed according to the position of the second concave parts 15A, 15B.

What is claimed is:

1. An electrochemical sensor, comprising:
    a base plate having a top surface and a bottom surface opposite of the top surface, the base plate includes a top concave part formed on the top surface;
    a fluid channel formed in the base plate, the fluid channel being a through-hole formed at a center of the top concave part in planar view, and formed in a direction that is orthogonal to the base plate to communicate a bottom part of the top concave part with the bottom surface opposite of the bottom part of the top concave part;
    a plurality of electrodes formed on the top concave part;
    a reagent fixed on the electrodes, having a ring-shape and disposed such that an inner edge of the ring-shape surrounds an opening of the through-hole;
    a cover which is directly provided on the base plate on which the plurality of electrodes are formed and is adapted to cover the top concave part; and
    an air channel disposed on the cover adapted to provide communication between an inside space existing between the top surface of the top concave part and the cover and an outside space above the cover.

2. The electrochemical sensor according to claim 1, wherein an outer edge shape in planar view of the top concave part is a triangle, a trapezoid, or a circle.

3. The electrochemical sensor according to claim 1, wherein the air channel includes at least one air hole formed in the cover.

4. The electrochemical sensor according to claim 3, wherein a planar view shape of the top concave part is formed in a triangle, and
    the air channel includes three air holes formed respectively at positions corresponding to apex portions of the triangle of the top concave part.

5. The electrochemical sensor according to claim 3, wherein a planar view shape of the top concave part is formed in a circle, and
    the air channel includes said at least one air hole formed on the cover and disposed so as to overlap with the fluid channel in a planar view state of the base plate.

6. The electrochemical sensor according to claim 1, further comprising:
    a pair of second concave parts formed around the top concave part,
    wherein the plurality of electrodes include:
    a first electrode pattern in which an electrode extending from the top concave part to one of the pair of second concave parts and an electrode lead part are formed integrally;
    a second electrode pattern which is insulated from the first electrode pattern, and in which an electrode extending from the top concave part to the other one of the pair of second concave parts and an electrode lead part are formed integrally;
    the cover has through-holes corresponding to positions of the second concave parts; and
    terminals for charging voltage to electrodes are inserted into the second concave parts through the through-holes of the cover.

7. The electrochemical sensor according to claim 1, wherein the bottom surface of the base plate is recessed inward.

8. The electrochemical sensor according to claim 1, wherein one of the plurality of electrodes is formed to at least partially surround the through-hole.

9. A lancet, comprising:

a lancet body;

a mounting part which is provided to the lancet body and to which an electrochemical sensor having top surface and a bottom surface is mounted in a state of the top surface facing the lancet body and the bottom surface facing outward; and a puncture needle configured to be freely advanced and retracted between a first position which is housed inside the lancet body and a second position which passes through a fluid channel of the electrochemical sensor mounted on the mounting part and protrudes from one of the top and bottom surfaces, the electrochemical sensor including:

a base plate provided with a top concave part formed on a top surface thereof;

a fluid channel formed in the base plate, the fluid channel being a through-hole formed at a center of the top concave part in planar view, formed in a direction that is orthogonal to the base plate, and adapted to be a communication channel between a bottom part of the top concave part and a bottom surface of the base plate opposite of the bottom part of the top concave part;

a plurality of electrodes formed on the top concave part;

a reagent fixed on the electrodes, having a ring-shape, and disposed such that an inner edge of the ring-shape surrounds an opening of the through-hole;

a cover which is directly provided on the base plate on which the plurality of electrodes are formed and covers the top concave part; and an air channel disposed on the cover adapted to provide communication between an inside space existing between the top surface of the top concave part and the cover and an outside space above the cover.

10. The lancet according to claim 9, wherein negative pressure for causing a fluid to flow from the bottom surface to the top surface of the base plate via the fluid channel in the base plate is applied to the fluid channel when a tip part of the puncture needle is retracted from the second position to the first position.

11. The lancet according to claim 9, wherein the electrochemical sensor is mounted on the mounting part in a state of becoming integral with the lancet body.

12. The lancet according to claim 9, wherein one of the plurality of electrodes is formed to at least partially surround the through-hole.

13. A bodily fluid measuring apparatus which is able to be equipped with a lancet, comprising:

a plurality of terminals which come in contact with respective ones of a plurality of electrodes of an electrochemical sensor mounted on the lancet;

an electronic circuit adapted to obtain a measurement signal via the plurality of terminals; and a drive mechanism adapted to advance and retract a puncture tool, the electrochemical sensor including:

a base plate provided with a top concave part formed on a top surface thereof;

a fluid channel formed in the base plate, the fluid channel being a through-hole formed at the center of the top concave part in planar view, formed in a direction that is orthogonal to the base plate, and adapted to be a communication channel between a bottom part of the top concave part and the bottom surface opposite of the bottom part of the top concave part;

a plurality of electrodes formed on the top concave part;

a reagent fixed on the electrodes, having a ring-shape and disposed such that an inner edge of the ring-shape surrounds an opening of the through-hole;

a cover which is directly provided on the base plate on which the plurality of electrodes are formed and is adapted to cover the top concave part; and an air channel disposed on the cover and adapted to provide communication between an inside space existing between the top surface of the top concave part and the cover and an outside space above the cover, and the lancet including:

a lancet body;

a mounting part which is provided to the lancet body and to which the electrochemical sensor is mounted in a state of the top concave part facing the lancet body and the bottom surface facing outward; and a puncture needle configured to be freely advanced and retracted between a first position which is housed inside the lancet body and a second position which passes through the fluid channel of the electrochemical sensor mounted on the mounting part and protrudes from one of the top and bottom surfaces.

14. The bodily fluid measuring apparatus according to claim 13, wherein one of the plurality of electrodes is formed to at least partially surround the through-hole.

* * * * *